United States Patent [19]
Allen et al.

[11] Patent Number: 5,037,416
[45] Date of Patent: Aug. 6, 1991

[54] DISPOSABLE ABSORBENT ARTICLE HAVING ELASTICALLY EXTENSIBLE TOPSHEET

[75] Inventors: Patrick J. Allen, Cincinnati; Mary E. Freeland, Norwood, both of Ohio

[73] Assignee: The Procter & Gamble Company, Cincinnati, Ohio

[21] Appl. No.: 321,813

[22] Filed: Mar. 9, 1989

[51] Int. Cl.$^5$ .................................. A61F 13/15
[52] U.S. Cl. ........................ 604/385.1; 604/385.2
[58] Field of Search ...................... 604/385.1, 385.2

[56] References Cited

U.S. PATENT DOCUMENTS

| | | | |
|---|---|---|---|
| 3,316,136 | 4/1967 | Pufahl | 156/160 |
| 3,886,941 | 6/1975 | Duane et al. | 604/385.1 |
| 3,948,702 | 4/1976 | Theissen | 156/278 |
| 3,949,128 | 4/1976 | Ostermeier | 428/152 |
| 3,987,794 | 10/1976 | Schaar | 128/287 |
| 4,014,338 | 3/1977 | Schaar | 128/287 |
| 4,036,233 | 7/1977 | Kozak | 604/389 |
| 4,096,163 | 10/1981 | Emi et al. | 428/212 |
| 4,205,679 | 6/1980 | Repke et al. | 604/370 |
| 4,209,563 | 6/1980 | Sisson | 428/288 |
| 4,333,782 | 6/1982 | Pieniak | 156/164 |
| 4,381,781 | 5/1983 | Sciarafa et al. | 604/372 |
| 4,418,123 | 12/1983 | Bunnelle et al. | 428/517 |
| 4,450,026 | 5/1984 | Pieniak et al. | 156/164 |
| 4,486,192 | 12/1984 | Sigl | 604/385.1 |
| 4,496,360 | 1/1985 | Joffe et al. | 604/385.1 |
| 4,525,407 | 6/1985 | Ness | 428/138 |
| 4,543,099 | 9/1985 | Bunnelle et al. | 604/385.1 |
| 4,556,596 | 12/1985 | Meuli | 428/152 |
| 4,655,760 | 4/1987 | Morman et al. | 604/385.2 |
| 4,710,187 | 12/1987 | Boland et al. | 604/385.1 |
| 4,731,066 | 3/1988 | Korpman | 604/366 |
| 4,789,699 | 12/1988 | Kieffer et al. | 524/271 |
| 4,895,568 | 7/1990 | Enloe | 604/385.2 |
| 4,940,464 | 7/1990 | Van Gompel | 604/396 |

FOREIGN PATENT DOCUMENTS 0137201 10/1980 Japan ................... 604/385.1

Primary Examiner—Randall L. Green
Assistant Examiner—David H. Willse
Attorney, Agent, or Firm—Larry L. Huston; Steven W. Miller; Richard C. Witte

[57] ABSTRACT

A disposable absorbent article, such as a diaper, is disclosed. The topsheet of the diaper is elastically extensible and provides a relatively low contact pressure against the skin of the wearer at relatively high elongations. This arrangement provides a diaper topsheet which can be elongated to conform to the shape of the wearer without causing undue discomfort or irritation. The relatively low ultimate contact pressure at relatively high elongation may be accomplished either through a low contact force differential material, or through a material which exhibits stress relaxation over a relatively short period of time. The topsheet may be a laminate having one elastomeric lamina and an inelastic lamina. Also disclosed is a method for making such a laminate.

13 Claims, 3 Drawing Sheets

DISPOSABLE ABSORBENT ARTICLE HAVING ELASTICALLY EXTENSIBLE TOPSHEET

FIELD OF THE INVENTION

The present invention relates to disposable absorbent articles, and more particularly to disposable absorbent articles having an elastically extensible topsheet.

BACKGROUND OF THE INVENTION

Disposable absorbent articles, such as diapers, frequently utilize elastically extensible components. For example, U.S. Pat. No. 3,860,003 issued Jan. 14, 1975 to Buell teaches an elastically contractible side portion for an integral disposable diaper. While the prior art addresses several properties of elastically extensible components, the prior art does not teach how to structure such components and tailor their properties to optimize wearer comfort and particularly how to maintain such optimization over a wide range of wearer sizes.

Several references are directed to the modulus of elasticity of components in a diaper. For example, U.S. Pat. No. 4,333,782 issued June 8, 1982 to Pieniak teaches a thin elastic film ribbon incorporated into the marginal edges of the diaper and having a modulus of elasticity less than 2,000 psi and preferably 75 to 400 psi. U.S. Pat. No. 4,450,026 issued May 22, 1984 to Pieniak et al. teaches a thin elastic film ribbon incorporated into the marginal edges of a diaper and preferably having a modulus of elasticity of 20 to 200 psi.

Other references in the prior art respecting disposable absorbent articles shows teachings directed to different properties of elastically extensible components. For example, U.S. Pat. No. 4,720,415 issued Jan. 19, 1988 to Vander Wielen et al. teaches a composite elastic material stretchable to an elongation of at least 25 percent of the relaxed length and which recovers at least 45 percent of the elongation upon release of the stretching force. U.S. Pat. No. 4,731,066 issued Mar. 15, 1988 to Korpman teaches a disposable diaper having a facing which is preferably 50 to 100 percent extensible and of relatively low rubber modulus.

However, none of the teachings of the prior art provide the benefits of the present invention, particularly a disposable absorbent article having an elastically extensible topsheet which has material properties tailored to optimize the comfort of the wearer. One particular property of an elastically extensible topsheet which affects wearer comfort is the contact pressure the topsheet exerts against the wearer while the disposable article is in use.

Accordingly, it is an object of this invention to utilize the topsheet of a disposable absorbent article to provide for wearer comfort and minimize the occurrence of red marking of the skin of the wearer. It is further an object of this invention to provide a disposable absorbent article having an elastically extensible topsheet which under a force of about 800 grams per centimeter (4.5 pounds per inch) of width is elongated about 50 to about 350 percent, without rupture.

SUMMARY OF THE INVENTION

The invention comprises a disposable absorbent article having a liquid impervious backsheet and a liquid pervious topsheet which is at least partially peripherally joined to the backsheet. An absorbent core is disposed intermediate the topsheet and the backsheet. The topsheet is elastically extensible in at least one direction, preferably between about 50 percent to about 350 percent elongation, without rupture, under a tensile load of about 800 grams per centimeter (4.5 pounds per inch) of width.

In one execution, the topsheet may have a differential force less than about 9 grams per centimeter of cumulative width of the elastic portion of the topsheet. In a second execution, the topsheet may exhibit a contact force of less than about 800 grams per centimeter of width after about 10 minutes at a temperature of at least about 22° C. when the topsheet is elongated within a range of about 50 to about 350 percent, i.e., the contact force is less than about 800 grams per centimeter of width throughout this range.

BRIEF DESCRIPTION OF THE DRAWINGS

While the Specification concludes with claims particularly pointing out and distinctly claiming the invention, it is believed the invention will be better understood from the following drawings taken in conjunction with the Specification. In the drawings like parts are designated with the same reference numeral and similar or analogous parts are designated with a prime symbol.

DETAILED DESCRIPTION OF THE INVENTION

Figure 1:
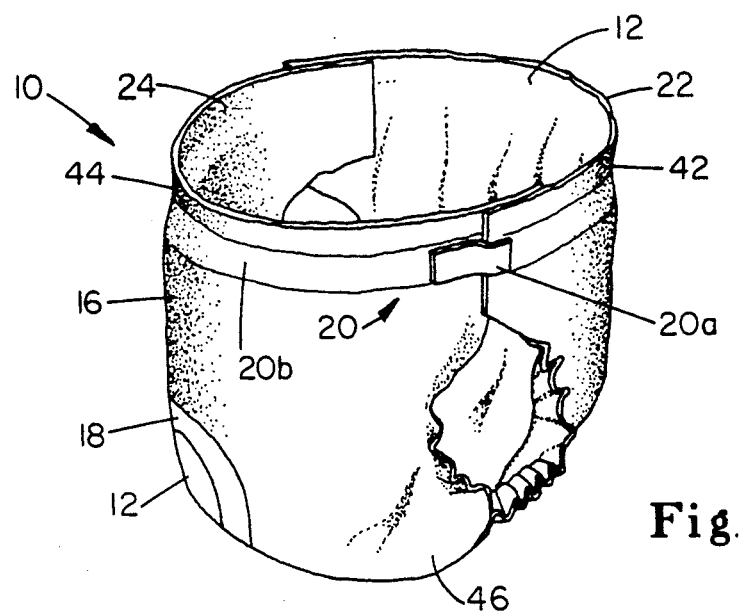
FIG. 1 is a perspective view of a disposable diaper of the present invention when assembled about a wearer, showing the core and backsheet partially in cutaway.

Referring to FIG. 1, there is shown a disposable absorbent article 10, intended to be worn about the lower torso. As used herein, the term "disposable absorbent article" refers to a garment which collects or contains body exudates and is intended to be discarded after a single use and not to be laundered or restored. A "disposable diaper" is a particular disposable article worn by infants or incontinent persons and which is drawn between the legs, and fastened about the waist of the wearer.

A preferred diaper 10 comprises a liquid pervious topsheet 12, a liquid impervious backsheet 16, and an absorbent core 18 disposed intermediate the topsheet 12 and the backsheet 16. The topsheet 12 and the backsheet 16 are at least partially peripherally joined to ensure the core 18 is held in the desired position.

Figure 2:
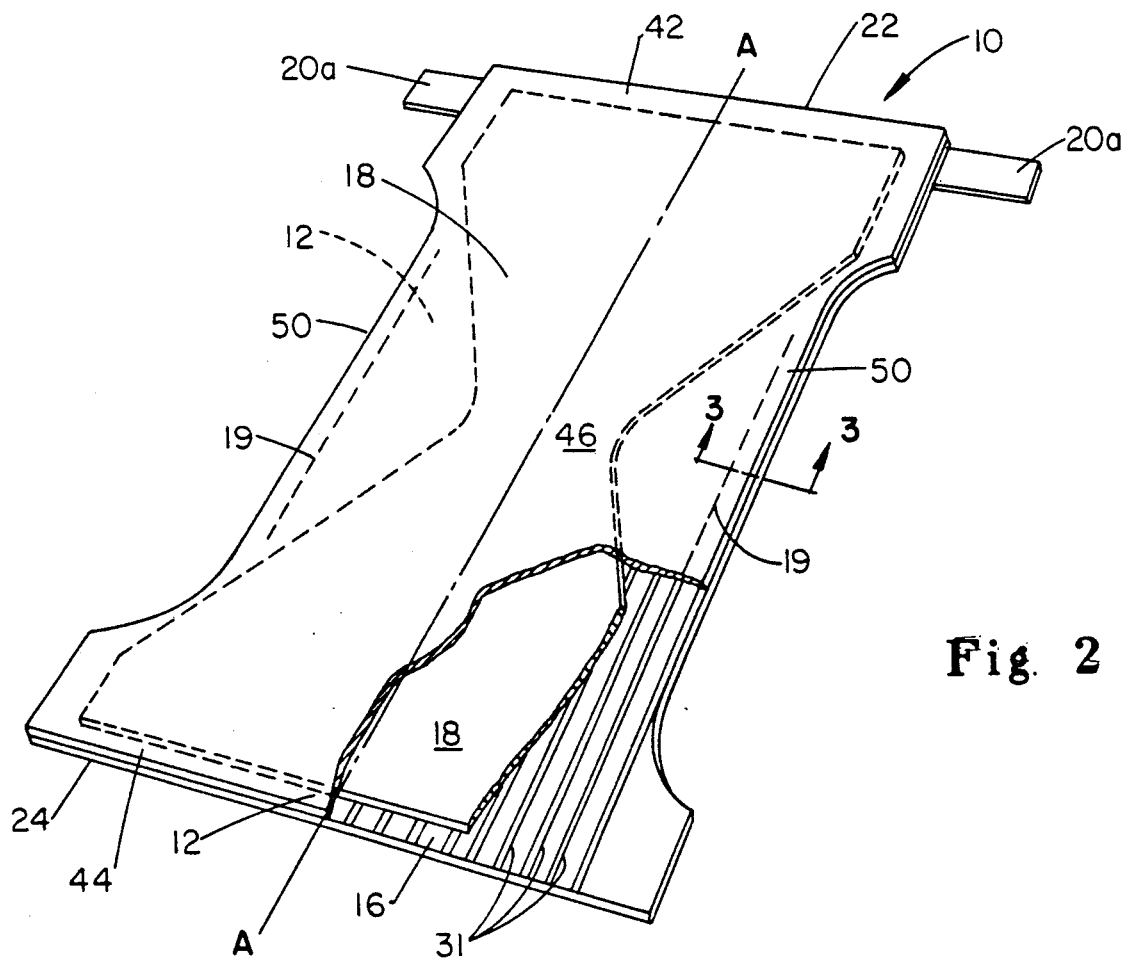
FIG. 2 is a top plan view of the diaper shown in FIG. 1 having no elastic induced contraction, showing the topsheet and core partially in cutaway.

As shown in FIG. 2, the topsheet 12 and the backsheet 16 generally define the periphery of the diaper 10. The periphery is the outer perimeter and greatest extent of the diaper 10. The periphery comprises a first end 22, a second end 24, and longitudinal marginal portions 50.

The diaper 10 has a first waist portion 42 and a second waist portion 44 extending respectively from the first end 22 and second end 24 of the diaper periphery towards the lateral center of the diaper 10 a distance of about one-fifth to about one-third the longitudinal length of the diaper 10. As used herein, the longitudinal dimension of the diaper 10 is that dimension which is aligned front to back with respect to the wearer as the diaper 10 is worn and parallels the longitudinal axis A—A. The waist portions 42 and 44 comprise those portions of the diaper 10 which, when worn, encircle the waist of the wearer and are generally at the highest elevation of the diaper 10 when the wearer is in the standing position. The crotch 46 of the diaper 10 is that portion of the diaper which is disposed between the first and second waist portions 42 and 44 and which, when worn, is positioned between the legs of the wearer.

The disposable diaper 10 may further comprise elastic members 19 and a fastening means 20 for fastening the diaper 10 about the waist of the wearer. The elastic members 19 are joined to the diaper 10 along both longitudinal marginal portions 50 so that the elastic members 19 hold the diaper 10 against the legs of the wearer. The fastening means 20 maintains the waist portions 42 and 44 of the diaper 10 in an overlapping configuration while the diaper 10 is worn. This arrangement fits the diaper 10 to the wearer and forms a side closure. The elements of the diaper 10 may be assembled in a variety of configurations well known to one skilled in the art, with a preferred configuration being generally described in U.S. Pat. No. 3,860,003 issued Jan. 14, 1975 to Buell, which patent is incorporated herein by reference for the purpose of disclosing a well known and preferred diaper 10 configuration.

Referring to FIG. 2, and examining the components of the diaper 10 in more detail, the topsheet 12 and backsheet 16 of the diaper 10 are generally coextensive and at least partially peripherally joined together as noted above. As used herein, the term "join" refers to the condition where a first member or component is affixed or connected to a second member or component, either directly or indirectly, where the first member or component is affixed or connected to an intermediate member or component which, in turn, is affixed or connected to the second member or component. The association between the first member or component and the second member or component is intended to remain for the life of the article. Joining of the topsheet 12 and the backsheet 16 to and throughout the absorbent core 18 is generally desirable. A tissue layer having a basis weight of approximately 16 grams per square meter (10 pounds per 3,000 square feet) and an air permeability of approximately 30 cubic meter per minute per square meter (100 cubic feet per minute per square foot) at a differential pressure of 13 millimeters (0.5 inch) of water works well.

The absorbent core 18 may assume a wide variety of sizes and shapes, such as rectangular or, as shown, be hourglass shaped. The absorbent core 18 may be made from a variety of commonly used materials such as comminuted wood pulp, typically referred to as airfelt. If desired, the absorbent core 18 may further contain absorbent gelling materials as is commonly used in the art.

The absorbent core 18 is superimposed on the backsheet 16 and preferably joined thereto by any means well known in the art, such as adhesive bonding. In a particularly preferred embodiment, adhesive bonding is accomplished by longitudinally oriented adhesive bands 31 which join the core 18 to the backsheet 16.

The backsheet 16 is impervious to liquids, such as urine, and prevents liquids absorbed by and contained in the absorbent core 18 from wetting undergarments, clothing, bedding and other objects which contact the diaper 10. As used herein, the term "backsheet" refers to any barrier disposed outwardly of the core 18 as the diaper is worn and which contains absorbed liquids within the diaper 10. Preferably, the backsheet 16 is a polyolefinic film of about 0.01 to about 0.051 millimeters (0.0005–0.002 inches) in thickness. A polyethylene film is particularly preferred, with a suitable film being manufactured by the Clopay Company of Cincinnati, Ohio and marketed as Film No. P18-850. If desired, the backsheet 16 may be embossed or matte finished to provide a clothlike appearance or be provided with passages to permit escape of vapors.

The elastic members 19 are operatively associated with both longitudinal portions 50 and the crotch 46 of the diaper 10 in an elastically contractible condition, so that in the normally unrestrained configuration, the elastic members 19 gather or contract the longitudinal marginal portions 50. As used herein, the term "operatively associated with" refers to the condition of two or more separate or individual components which act together. A particularly preferred diaper construction incorporating elastic members is described in detail in U.S. Pat. No. 3,860,003, referenced hereinbefore. Further, a method and apparatus suitable for manufacturing a disposable diaper having legbands with elastic members 19 is described in U.S. Pat. No. 4,081,301 issued Mar. 28, 1978 to Buell and which patent is incorporated herein by reference for the purpose of illustrating how such a diaper may be manufactured.

In a preferred embodiment of FIGS. 1 and 2, the elastic members 19 are associated with both longitudinal marginal portions 50 of the crotch portion 46 of the diaper 10. The elastic members 19 are joined to the longitudinal marginal portions 50, and particularly to the backsheet 16, to cause the longitudinal marginal portions 50 to be contracted. The elastic members 19 may be joined to a portion of the backsheet 16 in at least two manners. The elastic members 19 may be joined, while under tension, to the uncontracted longitudinal marginal portions 50. Alternatively, the longitudinal marginal portions 50 of the backsheet may be contracted (e.g., by pleating) and unstretched elastic members 19 joined to the contracted longitudinal marginal portions 50.

The elastic members may be adhesively joined to the backsheet, ultrasonically bonded, or heat/pressure sealed using a variety of bonding patterns. Preferably, the elastic members are adhesively joined to the longitudinal marginal portions 50 of the backsheet 16. If adhesively joined, the adhesive should be flexible and provide sufficient adhesion to hold each elastic member 19 to the backsheet 16 while the elastic member 19 is under tension. An adhesive which has been used with satisfactory results is manufactured by Findley Adhesives Corporation of Wauwatosa, Wis. and marketed under the tradename Findley 581-334-01.

Suitable elastic members 19 may be manufactured from a variety of elastomeric materials such as natural rubber, or elastomeric films such as Kraton, ethylene propylene-dimonomer, polyurethane, elastomeric foams, formed elastic scrim, or heat shrinkable material. The elastic members 19 may be a single strand of elastic material or several parallel or nonparallel strands of elastic material, and may be rectilinear or curvilinear.

Preferably, each elastic member 19 produces a tensile force of about 100 grams when stretched about 100 percent from the free length. A material which has been found to work well as an elastic member 19 is elastic tape having a cross section of about 0.18 by about 0.64 millimeters (0.007 by 0.025 inches) and is manufactured from natural rubber. A suitable material for the elastic member 19 is marketed by the Easthampton Rubber Thread Company under the tradename L-1900 rubber compound.

As noted above, preferably the diaper 10 is provided with a fastening means 20, which comprises a fastening system 20a and a complementary receiving surface 20b, for maintaining the first waist portion 42 and the second waist portion 44 in an overlapping configuration while the diaper 10 is worn. This arrangement secures the diaper 10 to the wearer.

The fastening system 20a and the receiving surface 20b should interact to resist the separation forces which occur while the diaper 10 is worn. The term "separation forces" refers to forces acting on the fastening means 20 which tend to cause separation, release or removal of the fastening system 20a from the receiving surface 20b. Separation forces include both shear and peel forces. The term "shear force" refers to distributive forces acting generally tangential to the plane of the fastening system 20a and the receiving surface 20b and which may be thought of as being generally parallel to the plane of the fastening means 20. The term "peel force" refers to distributive forces acting in the direction away from the wearer as the diaper 10 is worn and may be thought of as having a component perpendicular to the plane of the fastening means 20.

Separation forces are typically generated by movements of the wearer or by the wearer trying to unfasten the diaper 10. Generally, an infant should not be able to unfasten or remove a diaper 10 that the infant is wearing, nor should the diaper 10 become unfastened in the presence of ordinary separation forces which occur during normal wearing periods. However, an adult should be able to remove the diaper 10 to change it when soiled or inspect the diaper 10 to see if soiling has occurred. Generally, the fastening system 20a and the receiving surface 20b should preferably resist a peel force of at least about 200 grams, more preferably at least about 500 grams and even more preferably at least about 700 grams. The fastening system 20a and the receiving surface 20b should preferably resist a shear force of at least about 500 grams, more preferably at least about 750 grams, and even more preferably at least about 1,000 grams.

The receiving surface 20b may be disposed in a first position anywhere on the diaper 10, as long as the receiving surface 20b engages the fastening system 20a to maintain the first and second waist portions 42 and 44 in an overlapping configuration. For example, the receiving surface 20b may be disposed on the outside surface of the second waist portion 44, on the inside surface of the first waist portion 42, or any other position on the diaper 10 on which the receiving surface 20b is disposed so as to engage the fastening system 20a. The receiving surface 20b may be integral, a discrete element joined to the diaper 10, or a portion of the diaper 10, such as the topsheet 12 or the backsheet 16.

Suitable fastening means 20 include adhesive tapes and refastenable mechanical fastening systems 20. If an adhesive tape fastening means 20 is selected, a preferred construction has a generally Y-shaped cross-section and is shown in U.S. Pat. No. 3,848,594 issued Nov. 19, 1974 to Buell, which patent is incorporated herein by reference for the purpose of showing a suitable adhesive tape fastening system 20a. If a refastenable mechanical fastening means 20 is selected from a preferred construction is shown in U.S. Pat. No. 4,846,815 issued July 11, 1989 in the name of Scripps, which patent is incorporated herein by reference for the purpose of describing a particularly preferred refastenable mechanical fastening means 20.

The topsheet 12 is preferably compliant, tactilely pleasant and nonirritating to the skin of the wearer. The topsheet 12 prevents contact of the absorbent core 18 and liquids therein with the skin of the wearer. The topsheet 12 is liquid pervious, permitting liquids, particularly urine, to readily penetrate therethrough. As used herein, the term "topsheet" refers to any liquid pervious facing which contacts the skin of the wearer while the diaper 10 is worn and prevents substantial contact of the core 18 with the skin of the wearer. A topsheet 12 is considered liquid pervious if it has a liquid strike-through time as described in the Edana test 150.0–84 of about less than 8 seconds or preferably about less than 3 seconds.

Figure 3:
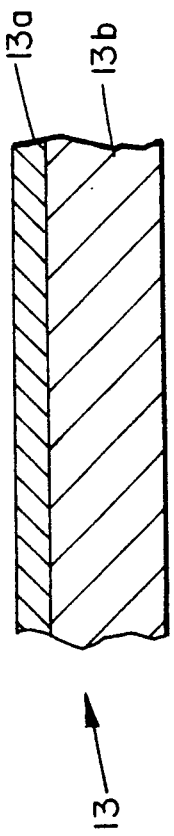
FIG. 3 is a fragmentary vertical sectional view of the topsheet of the diaper of FIGS. 1 and 2 taken along line 3—3 of FIG. 2.

As shown in FIG. 3, the topsheet 12 may be made of a laminate 13 having at least two laminae 13a and 13b. Lamina 13b faces the wearer and may be made from woven, nonwoven, spunbonded or carded materials. A preferred topsheet lamina 13b is carded and thermally bonded by means known to those skilled in the nonwoven fabrics art. A particularly preferred topsheet lamina 13b has a weight of about 4 to about 25 grams per square meter, a minimum dry tensile strength of about 87 grams per centimeter in the machine direction and a wet tensile strength of at least about 8 grams per centimeter in the cross-machine direction. Lamina 13a faces the absorbent core 18 and controls the ultimate contact pressure within the specified ranges of elongation.

Referring back to FIG. 2, the topsheet 12 may be peripherally joined to the backsheet 16 in any suitable manner as is well known in the art. The topsheet 12 is preferably continuously peripherally joined to the backsheet 16, although any embodiment in which the topsheet 12 is at least partially peripherally joined to the backsheet 16 sufficient to prevent disruption of the arrangement described herein is adequate. In a preferred embodiment, a multiplicity of longitudinal adhesive bands 31, preferably of hot melt adhesive are applied to the backsheet 16, generally parallel to the longitudinal axis A—A of the diaper 10. The longitudinal adhesive bands 31 join the topsheet 12 to the backsheet 16 at a location dependent upon the spacing between such longitudinal adhesive bands 31, and the distance which the topsheet 12 and backsheet 16 extend beyond the absorbent core 18. The adhesive should be sufficient to securely join the topsheet 12 to the backsheet 16 in the peripheral marginal area disposed outboard of the absorbent core 18. A suitable hot melt adhesive is manufactured by the Eastman Chemical Products Company of Kingsport, Tenn. and marketed under the tradename Eastobond A-3.

In accordance with one aspect of the present invention, the topsheet 12 is elastically extensible in at least one direction. As used herein, the term "elastically extensible" means able to be stretched from the free length at least about 50 percent for a period of about 15 seconds and to return to within about 10 percent of the free length within about 5 minutes of the release of the force which causes such elongation to occur. Generally the principal axis of elongation, in which the laminate 13 of the topsheet 12 is elastically extensible is generally parallel to the longitudinal axis A—A, although all or a portion of the topsheet may be elastically extensible in more than one direction or in a direction generally orthogonal the longitudinal axis A—A.

Preferably, the topsheet 12 of the present invention is elastically extensible to at least about 350 percent elongation without rupture and more preferably to at least about 450 percent elongation without rupture, although a topsheet 12 which has a lesser elongation without rupture, such as 50 to 100 percent is suitable. As used herein, the term "rupture" means tearing, fracturing, or breaking into two or more subparts. This property provides for conforming to the shape of the wearer's body and maintaining close contact to the skin of the wearer. Also a topsheet 12 which is relatively highly extensible can comfortably fit a larger range of sizes of wearers.

To prevent excessive forces from occurring when the topsheet 12 is stretched about the body of the wearer, the topsheet 12 has a contact force of less than about 800 grams per centimeter (4.5 pounds per inch) of width upon elongation of about 50 to about 350 percent. As used herein, the term "contact force" refers to the highest reading obtained on a tensile machine when a one centimeter wide sample of the topsheet 12 is pulled throughout the specified range of elongation as described below. As used herein, the term "elongation" refers to change in length from the free length. For example, a sample which is extended to 100 percent elongation is twice the free length of the original sample.

More preferably, the topsheet 12 has a contact force less than about 800 grams per centimeter (4.5 pounds per inch) of width when elongated about 50 to about 350 percent and even more preferably, a contact force of less than about 240 grams per centimeter (1.34 pounds per inch) of width when elongated about 100 to about 300 percent. As used herein the phrase "grams per centimeter of width" refers to the ratio of the highest reading from the tensile machine, in grams, when the sample is tested as described below; to the width of the sample, the gage length being taken parallel to the principal axis of elongation, if the sample is orthotropic or anisotropic.

The sample of the topsheet 12 has a 1 centimeter width. If the topsheet 12 has inelastic zones, a sample having a 1 centimeter cumulative width of elastic zones is selected. It will be apparent that if a sample having a cumulative width of elastic zones of other than 1 centimeter is selected the tensile loading should be normalized to a 1 centimeter cumulative elastic sample width.

The contact force may be measured using a Instron Model 1122 tensile machine made by the Instron Corporation of Canton, Mass. utilizing constant rate of elongation cross heads traveling at a separation speed of about 50.8 centimeters per minute (20 inches per minute). A sample of any convenient gage length having a one centimeter width taken perpendicular the principal axis of elongation of the topsheet 12 is selected.

The sample is placed in the tensile machine and elongated, in tension, until a reading of about 800 grams is obtained. The resulting elongation at such a load is then noted. A one centimeter wide sample is taken from a topsheet 12 according to the present invention having a relatively low contact force differential. A preferred topsheet 12 has a contact force differential less than about 7,030 kilograms per square meter (10 pounds per square inch), and a particularly preferred topsheet 12 has a contact force differential less than about 3,520 kilograms per square meter (5 pounds per square inch). As used herein, the term "contact force differential" is defined by the formula: $E = (F/A)/(\Delta L/L_O)$, wherein E is the Young's modulus of elasticity in tension, herein referred to as the "contact force differential", F is the applied elongation force in kilograms, A is the cross-sectional area of the sample prior to elongation in square meters, $\Delta L$ is the change in elongation from the free length in meters or any other convenient units, and $L_O$ is the original gage length of the sample measured in meters or any other convenient units of length, coincident with the units utilized to measure the change in elongation from the free length. The area A is the product of the sample width and thickness, or may be found by back calculating from the mass and density of the sample if the surface is irregular or the thickness is otherwise difficult to measure. The initial length and change in length are easily found using known techniques and instrumentation. The contact force differential may be thought of as the slope of the stress-strain curve taken within the range of elongation under consideration.

The differential force per 50 percent increment of elongation may be determined as follows. The sample of the topsheet 12 is loaded into a tensile machine, as described above. The sample is elongated, in tension until the gage length is increased approximately 50 percent and the resultant reading in grams, from the tensile machine, is recorded and divided by the original, unstretched, cumulative width of the topsheet 12. This calculation yields a first force measured in grams per centimeter. The sample is then further elongated, in tension, until an elongation of 100 percent from the free length is obtained. Again the resultant reading in grams, from the tensile machine, is recorded and divided by the original, unstretched, cumulative width of the topsheet 12. This calculation yields a second force in grams per centimeter. The first force is subtracted from the second force, yielding a "differential force" per 50 percent increment of elongation having units of grams per centimeter. This procedure is repeated, in 50 percent increments, until the fully extended length of any lamina 13a, 13b, or 13c of the laminate 13 or 350 percent elongation is reached.

All tensile readings should preferably be taken within about 5 seconds of reaching the desired elongation. A strip chart recorder may advantageously be utilized to obtain the readings which occur when the sample reaches the desired elongation.

A topsheet 12 according to the present invention may have a differential force per 50 percent elongation of less than about 9 grams per centimeter of cumulative elastic width of the topsheet 12 and more preferably less than about 6 grams per centimeter of cumulative elastic width of the topsheet 12.

Alternatively, the aforementioned ultimate contact force within the desired range of elongations may be obtained through stress relaxation of the topsheet 12. As used herein, the term "stress relaxation" refers to the dissipation and diminution of stresses and the associated contractive and restoring forces which occur over time when a sample is elongated from its free length. Stress relaxation may be enhanced by application of heat or may occur due to elongation of the topsheet 12 to a range which causes slip of the molecular structure to occur. It is desired that the stress relaxation occur after a relatively short period of time from initial elongation of the topsheet 12—so that the wearer does not experience discomfort caused by high contractive forces of the topsheet 12 for an undue length of time. A topsheet 12 which exhibits a contact force of less than about 800 grams per centimeter (4.5 pounds per inch) of width, when tested as described above, after a period of at least at least about 10 minutes at a temperature of at least about 22° C. when elongated to a range of about 50 to about 350 percent is suitable. The contact force is preferably less than about 800 grams per centimeter (4.5 pounds per inch) of width throughout the entire range of elongation, and more preferably less than about 400 grams per centimeter (2.25 pounds per inch) of width throughout this range.

Referring back to FIG. 3, one topsheet 12 which is suitable for use with the present invention is a laminate 13 having two laminae 13a and 13b. The first lamina 13a is elastically extensible, faces the core 18 joined in face-to-face relation with a relatively inextensible second lamina 13b which faces the wearer.

The first lamina 13a is preferably elastomeric and more preferably an elastomeric adhesive. A pressure sensitive elastomeric adhesive is particularly preferred for the first lamina 13a, so that it may be readily joined to the second lamina 13b to form a unitary laminate 13. The adhesive selected for the first lamina 13a should also be capable of elongation from about 50 to about 350 percent in one or two principal directions without rupture, not exhibit excessive necking or thinning when elongated, or exhibit excessive hysteresis or delamination upon cycling. Within the desired range of elongations, the contact force differential of the lamina 13a generally controls the contact force differential of the laminate 13, due to the second lamina 13b being generally relatively inextensible. The first lamina 13a may be omitted from the urine acquiring zone of the topsheet 12, to ensure the topsheet 12 is liquid pervious.

The second lamina 13b may be any flexible nonwoven fabric, apertured formed film, or any material commonly used in the art as a topsheet 12. A preferred second lamina 13b is a polyolefinic nonwoven fabric having a basis weight of about 4.2 to about 25 grams per square meter (5 to 30 grams per square yard). A particularly preferred second lamina is made of polypropylene and manufactured by the Veratec Corporation of Walpole, Mass. and sold as Grade 149048.

The first lamina 13a of the laminate 13 is prestretched prior to joining of the first lamina 13a with the second lamina 13b. As noted above, after prestretching the lamina 13a, the pressure sensitive adhesive property of the first lamina 13a provides for continuous face-to-face joining of the first lamina 13a with the second lamina 13b. Upon release of the force which causes prestretching of the first lamina 13a, the resulting laminate 13 gathers or contracts in the direction of prestretching. The resulting laminate 13 will be elastically extensible to the limit of prestretching of the first lamina 13a. If the laminate 13 is elongated beyond the amount of prestretch of the first lamina 13a, the free length of the relatively inextensible second lamina 13b will be exceeded. If this should occur, the contact pressure will sharply increase without significant further elongation and rupture will likely occur. Therefore, the first lamina 13a should be prestretched at to at least the desired limit of elongation, as noted above, to obviate high ultimate contact pressures and rupture of the laminate 13. After rupture, the elastic properties of the first lamina 13a would control further elongation.

If the first lamina 13a is prestretched in two principal directions, the resulting laminate 13 will contract in both such directions, proportional to the magnitude of prestretching in each principal direction. However, a laminate 13 which is only longitudinally extensible has been found to work well as a topsheet 12. The resulting laminate 13 is elastically extensible without rupture until at least the free length of the second lamina 13b is reached.

If the first lamina 13a comprises a hot melt adhesive, the hot melt adhesive of the first lamina 13a should have a viscosity of about 9,000 to about 45,000 centipoises at a temperature of about 176° C., as measured by ASTM Standard D 3236-73. Pressure sensitive elastomeric adhesive marketed by the Findley Adhesives Corporation of Wauwatosa, Wis. under the tradename 198-338 has been found to be particularly well suited for this purpose.

Figure 4:
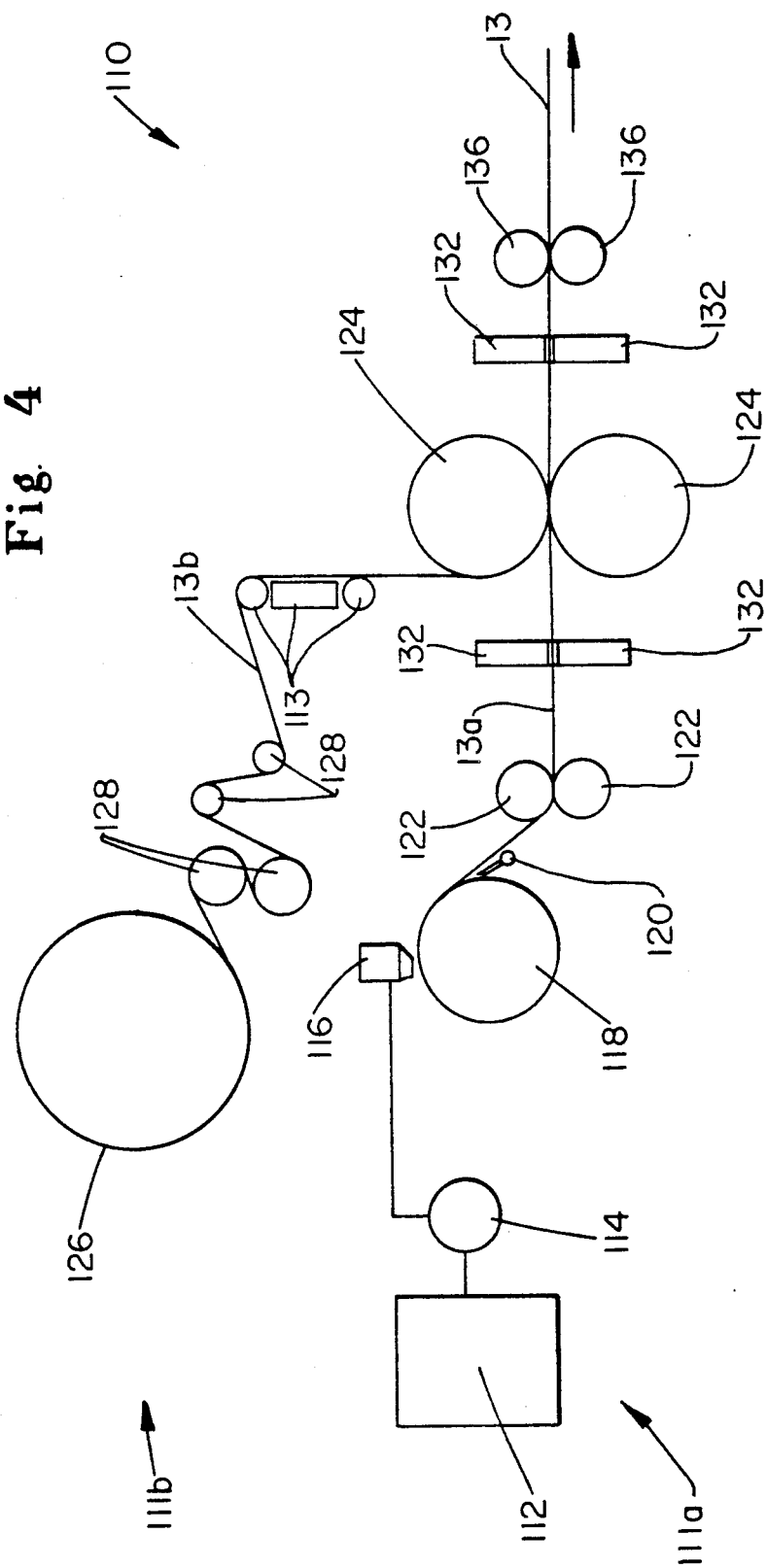
FIG. 4 is a side elevational schematic view of one apparatus which may be used to manufacture the topsheet of the present invention.

Referring to FIG. 4, the laminate 13 of the topsheet 12 of the present invention may be produced on the illustrated apparatus 110. The apparatus 110 comprises separate lines 111a and 111b for each of the laminae 13a and 13b. The first line 111a, utilized for the first lamina 13a, comprises an adhesive tank 112 used for storage of the hot melt adhesive supply, a pump 114 to transport the adhesive, an extrusion head 116 and a chill roll 118 to form the web of the first lamina 13a. The second lamina 13b is formed on the second line 111b and is taken from an unwind roll through tensioning rolls 128 and, if desired, a tracking system 113. The combining rolls 124 join the confluent laminae 13a and 13b into a unitary laminate 13.

Examining FIG. 4 in more detail, the apparatus 110 comprises the means for joining at least two laminae, 13a and 13b in face-to-face relation. The first lamina 13a is formed from a supply of hot melt adhesive contained in the adhesive tank 112. The adhesive tank 112 is heated to maintain the hot melt adhesive of the first lamina 13a at a temperature of about 170 to about 80° C. The adhesive tank is connected to a pump 114 designed to extract adhesive from the heated adhesive tank 112 without imparting excessive shear to the adhesive. A metering gear pump 114 has been found to be suitable for this purpose. Preferably, the adhesive is not recirculated while in the adhesive tank 112, or otherwise, to prevent excessive shear from being applied to the material of the lamina 13a. Excessive shear may cause molecular breakdown of the material, resulting in a material of lower contact pressure.

The metering gear pump 114 supplies the adhesive, under pressure, to the extrusion head 116. The extrusion head 116 has a slot through which the molten elastic adhesive of the first lamina 13a is extruded to form a thin film of about 0.03 to about 1.0 millimeters (0.001-0.04 inches) in thickness, and of any desired width, onto the chill roll 118. A first lamina 13a of about 0.0084 grams per square centimeter is suitable. It will be apparent to one skilled in the art that increasing the thickness of the elastomeric lamina 13a will provide a proportional increase in the ultimate contact pressure of the laminate 13 of the topsheet 12.

The chill roll 118 cools the extruded adhesive of the first lamina 13a into a web of the laminate 13 suitable for further processing. The web of the first lamina 13a is separated from the chill roll by a doctor blade 120. If desired, a second roll (not shown) may be utilized in conjunction with the chill roll 118 to provide additional cooling and a nip for compression of the web of the first lamina 13.

The first lamina 13a is then drawn through a nip formed between tensioning rolls 122. The tensioning rolls 122 provide for proper takeoff speed of the first lamina 13a from the chill roll 118 and further provide for proper entry of the first lamina 13a into the combining rolls 124.

The second lamina 13b is taken from the unwind roll 126 and preferably passes through S-wrap tensioning rolls 128 to provide for proper tensioning and prevent puckering or bunching of the second lamina 13b. If necessary, a tracking system 130, as is commonly utilized and known in the art, may be employed to optimally track and adjust the web of second lamina 13b into the combining rolls 124. A tracking system manufactured by the Fife Corporation of Oklahoma City, Okla. and sold as a Fife Guide Model No. OP6 LRA has been found to work well.

The laminae 13a and 13b enter the combining rolls 124 generally parallel to the travel of the laminate 13 as it passes through the nip of the combining rolls 124.

After the laminate 13 leaves the nip of the combining rolls 124, the exposed face of the first lamina 13a may be deactivated, by blocking as is commonly known in the art, so that the adhesive of the first lamina 13a does not bond to other materials through the pressure sensitive properties of the adhesive of the lamina 13a. Blocking is accomplished by the adhesive deactivation system 132 applying a powder of resin to the exposed face of the lamina 13a. Suitable resin powders include talcum powder, polyolefinic powders, and preferably a resin similar to that used for the second lamina 13b. If desired, the adhesive deactivation system 132 may be applied to the exposed face of the first lamina 13a prior to the first lamina 13a entering the nip of the combining rolls 124.

If desired, a rotary knife (not shown) may be provided intermediate the chill roll 118 and the combining rolls 124 to selectively remove portions of the first lamina 13a, but not the second lamina 13b,—so that the topsheet 12 is urine pervious. The rotary knife may be cooled to help prevent the cutting edge from becoming blocked with molten adhesive. Any pattern which removes the first lamina 13a in the urine acquiring zone of the topsheet 12 is suitable.

If it is desired to place a liquid pervious zone in the topsheet 12 without the use of a rotary knife, two extrusion heads 116 may be provided and transversely registered, so that a zone having no first lamina 13a is produced therebetween. This arrangement produces a laminate 13 having two machine direction oriented outboard zones, each having two laminae 13a and 13b, and a liquid pervious central machine direction zone having only the second lamina 13b.

If desired, an additional second lamina (not shown) may be joined in face-to-face relation with the exposed and outwardly oriented face of the pressure sensitive adhesive first lamina 13a. This is accomplished by providing a second material unwind roll (not shown) and associated tension and tracking systems, similar to that used for the second lamina 13b but disposed on the opposite face of the first lamina 13a. The resulting laminate has three laminae, with the central lamina 13a being of pressure sensitive elastomeric adhesive and the outboard laminae being of relatively inextensible substrate materials. If desired, one or both of outboard laminae may be elastically extensible. The outboard laminae may be of similar or different materials, as desired. It will be apparent to one skilled in the art that an adhesive deactivation system 132, should not be employed prior to the combining rolls 124 if two outboard laminae are to be constructed according to the apparatus 110 of FIG. 4.

Figure 5:
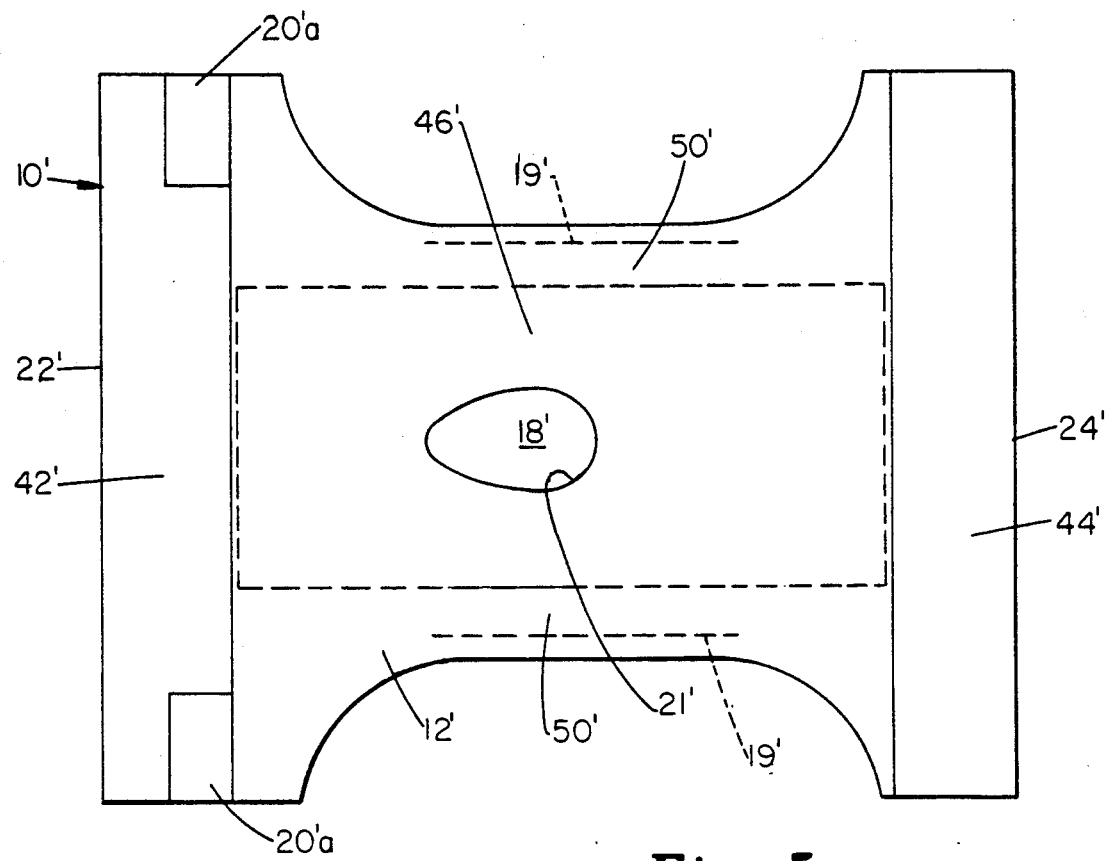
FIG. 5 is a top plan view of a second embodiment of a diaper having a passageway to allow communication of solid waste materials and incorporating a topsheet according to the present invention.

An alternative embodiment of a diaper 10' having a topsheet 12' according to the present invention is shown in FIG. 5. As described above, the alternative embodiment of a diaper 10' has an elastically extensible topsheet 12', a backsheet 16' and a rectangularly shaped absorbent core 18' disposed intermediate the topsheet 12 and the backsheet 16'. The alternative embodiment of a diaper 10' also has the fastening means 20 and the longitudinal marginal portions 50' discussed above. The alternative diaper 10' further comprises a passageway 21' associated with the topsheet 12' which passageway 21' permits communication of waste materials, particularly including but not limited to solid fecal materials through the topsheet 12' As used herein, a "passageway" is any opening which is sufficient to permit fecal material to pass through the topsheet 12' without significant obstruction.

In a preferred embodiment, the passageway 21' takes the form of an aperture. As used herein, the term "aperture" includes but is not limited to holes, slits and combinations thereof. Preferably, the aperture is an oblong hole having a doubly convex shape. If desired, the edges of the aperture 21' may be heat sealed to prevent delamination.

The size of the passageway 21' is a balance between the minimum size necessary to accommodate variations in the placement of the anus relative to the perineum and various cross-sections of solid fecal material, while minimizing undue skin contact with such waste materials. It is preferred that this passageway have a greater longitudinal than transverse dimension to ensure registration with the anal opening when the diaper 10' is placed onto the wearer in various longitudinal alignments.

Figure 6:
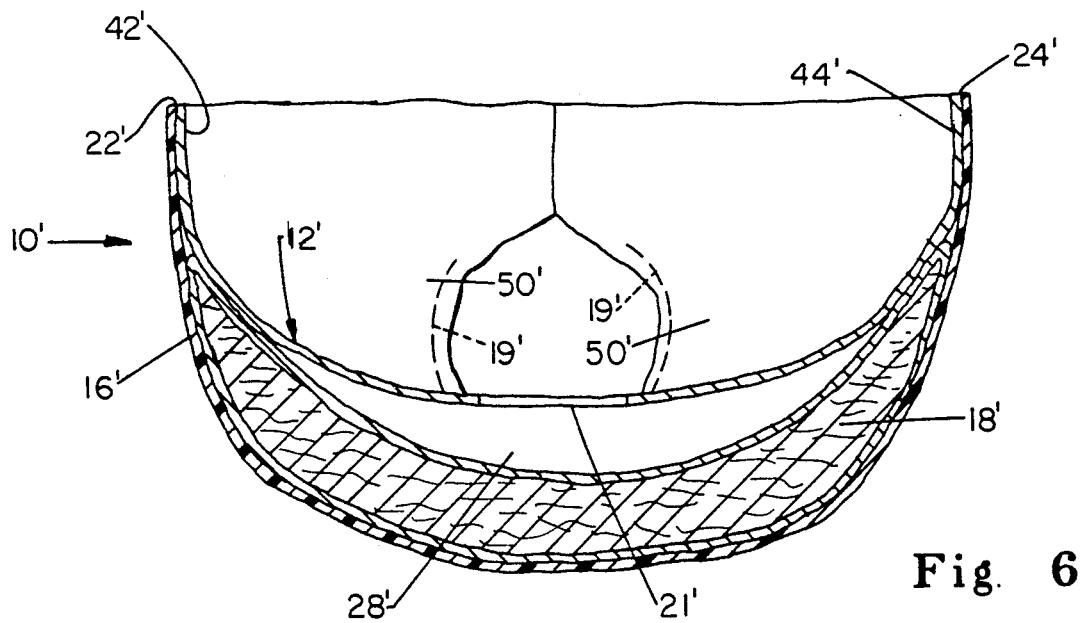
FIG. 6 is a vertical sectional view of the diaper of FIG. 5, when assembled about a wearer.

Referring to FIG. 6, upon communication through the topsheet 12' the waste materials enter a void space 28' between the topsheet 12' and absorbent core 18', thereby substantially isolating such waste materials from the skin of the wearer. The void space 28 between the topsheet 12' and the absorbent core 18' is created by longitudinally contracting or foreshortening the topsheet 12'. This arrangement enhances the conformability and shaping of the topsheet 12' to the buttocks of the wearer. The longitudinal contraction or foreshortening should be great enough to provide a snug fit and maintain such fit during various motions of and throughout the period worn by the wearer. However, the longitudinal contraction or foreshortening should not be so great as to yield a pressure which may cause red marking or irritation of the skin of the wearer.

The volume of the void space 28' is not critical, so long as at least about 90 grams of fecal material can be accommodated. Likewise, the shape of the void space 28' is not critical and indeed will be irregular. Preferably, the topsheet 12' is not affixed to the core 18' near the vicinity of the passageway 21', otherwise the capacity of the void space 28' may be reduced. If desired, the urine acquiring zone of the topsheet 12' may be joined to the absorbent core 18' to promote urine transmission through the topsheet 12'.

As shown in FIG. 6, when worn, ideally the longitudinally contracted or foreshortened topsheet 12' will generally conform to the wearer, while the larger radius of curvature of the absorbent core 18' allows the core 18' to fall away from the topsheet 12' and create the void space 28' thereinbetween. Alternatively stated, the differential radii of curvature of the topsheet 12' and the core 18' creates a shallow hole in the absorbent core 18', which hole collects waste materials and substantially isolates the collected waste materials from the wearer, helping to prevent epidermal irritation.

With continuing reference to FIG. 6, the topsheet 12' may be foreshortened relative to the balance of the diaper 10', by making the topsheet 12' longitudinally shorter than the absorbent core 18' and backsheet 16'. The topsheet 12' is at least partially peripherally joined to the backsheet 16' at the transverse edges in accordance with any of the well known joining means discussed above. Preferably, as discussed above, the topsheet 12' is totally peripherally affixed to the backsheet 16'. A greater differential longitudinal dimension between the topsheet 12' and backsheet 16' will generally provide a greater void space 28' volume If desired, the transverse margins 24' of the topsheet 12' to the backsheet 16'.

A topsheet 12' having the properties of the topsheet 12 discussed above relative to the diaper 10 of: elongation without rupture, ultimate contact pressure within the specified ranges of elongation, contact force differential and stress relaxation is particularly suitable for the diaper 10' of FIGS. 5 and 6. Such a topsheet 12' provides close and snug conformance of the topsheet 12' to the wearer, over a wide range of sizes of wearers, without exerting undue forces against the skin of the wearer and thereby causing discomfort and epidermal irritation.

It will be apparent to one skilled in the art that several variations in the invention disclosed herein are feasible without departure from the spirit and scope of the invention. For example, the topsheets 12 and 12', may have zones of differing elastic properties or may have inelastic zones. Inelastic zones may be created in the laminate 13 by a secondary heating process, such as heated rollers 136 that selectively provide localized heating to the zones of laminate 13 desired to be rendered inelastic.

Alternatively, a film of nonuniform thickness may be utilized for the second lamina 13b. As the thickness of the film increases, a greater force will be required for the same amount of extension to occur. If another second lamina 13b is disposed on the opposite (exposed) face of the first lamina 13a, reducing the contact force of the laminate 13 in the region having two opposed second laminae 13b. All such variations are within the spirit and scope of the present invention.

What is claimed is:

1. A disposable absorbent article comprising:
a liquid impervious backsheet;
a liquid pervious topsheet at least partially peripherally joined to said backsheet, wherein said topsheet is elastically extensible in at least one direction to an elongation greater than 50 percent and less than about 350 percent under a tensile load of about 800 grams per centimeter of width; and
an absorbent core disposed intermediate said topsheet and said backsheet.

2. A disposable absorbent article comprising:
a liquid impervious backsheet;
a liquid pervious topsheet at least partially peripherally joined to said backsheet, wherein said topsheet is elastically extensible in at least one direction to an elongation greater than 50 percent and less than about 350 percent under a tensile load of about 800 grams per centimeter of width and has a differential force per 50 percent increment of elongation less than about 9 grams per centimeter of said cumulative width; and
an absorbent core disposed intermediate said topsheet and said backsheet.

3. A disposable absorbent article comprising:
a liquid impervious backsheet;
a urine pervious topsheet at least partially peripherally joined to said backsheet, wherein said topsheet is elastically extensible in at least one direction to an elongation greater than 50 percent and less than about 350 percent under a tensile load of about 800 grams per centimeter of width and after about 10 minutes at a temperature of at least about 22° C.; and
an absorbent core disposed intermediate said topsheet and said backsheet.

4. A disposable absorbent article according to claim 1, 2 or 3, wherein said topsheet is comprised of a laminate having at least two laminae, wherein one lamina is elastically extensible and one lamina is relatively inextensible.

5. A disposable absorbent article according to claim 4, wherein said extensible lamina is an elastomeric film.

6. A disposable absorbent article according to claim 5, wherein said elastomeric film comprises a pressure sensitive adhesive.

7. A disposable absorbent article according to claim 1, 2 or 3, wherein said topsheet is elastically elongated between about 100 percent and about 300 percent under a tensile load of about 800 grams per centimeter of width.

8. A disposable absorbent article according to claim 2, wherein said topsheet has a differential force per 50 percent increment of elongation less than about 6 grams per centimeter of said cumulative width.

9. A disposable absorbent article according to claim 3, wherein said topsheet is elongated greater than 50 percent and less than about 100 percent under a tensile load of about 400 grams per centimeter of width after about 10 minutes at a temperature of at least about 22° C.

10. A disposable absorbent article according to claim 1, 2, or 3 further comprising a passageway through said topsheet.

11. A disposable absorbent article according to claim 1, 2, 3, or 8 wherein said topsheet is elongated without rupture throughout said range of elongation.

12. A disposable absorbent article comprising:
a liquid impervious backsheet;
a liquid pervious topsheet at least partially peripherally joined to said backsheet, wherein said topsheet is elastically extensible in at least one direction to an elongation greater than 50 percent and less than about 350 percent under a tensile load of about 400 grams per centimeter of width; and
an absorbent core disposed intermediate said topsheet and said backsheet.

13. A disposable absorbent article according to claim 12, wherein said topsheet is elongated between about 100 percent and about 300 percent under a tensile load of about 400 grams per centimeter of width.

* * * * *

UNITED STATES PATENT AND TRADEMARK OFFICE
CERTIFICATE OF CORRECTION

PATENT NO. : 5,037,416
DATED : August 6, 1991
INVENTOR(S) : Patrick J. Allen, M. Elaine Freeland It is certified that error appears in the above-indentified patent and that said Letters Patent is hereby corrected as shown below:

Column 6, line 7   "selected from a" should read ---selected, a---.

Column 9, line 22  "18 joined" should read ---18 and is joined---.

Column 9, line 47  "(5 to 30 grams" should read ---(3.3 to 21 grams---.

Column 10, line 43 "about 80°C." should read ---about 180°C.---.

Column 11, line 5  "lamina 13." should read ---lamina 13a.---.

Column 12, line 16 "means 20 and" should read ---means 20' and---.

Column 13, line 24 "topsheet 12' to the backsheet 16'." should read
                   ---topsheet 12' may be inelastic to provide for ease of
                   joining the topsheet 12' to the backsheet 16'.---.

Signed and Sealed this

Twenty-fifth Day of January, 1994

Attest:

BRUCE LEHMAN

Attesting Officer    Commissioner of Patents and Trademarks